(12) United States Patent
Moreno Perez et al.

(10) Patent No.: US 8,286,894 B2
(45) Date of Patent: Oct. 16, 2012

(54) CONTAINER FOR EVAPORATING VOLATILE SUBSTANCES AND METHOD OF MANUFACTURING SAID CONTAINER

(75) Inventors: David Moreno Perez, Barcelona (ES); Jose Antonio Munoz Martinez, Barcelona (ES); Ruben Garcia Fabrega, Barcelona (ES); Andrea Caserta, Barcelona (ES)

(73) Assignee: Zobele Espana, S.A., Barcelona (ES)

( * ) Notice: Subject to any disclaimer, the term of this patent is extended or adjusted under 35 U.S.C. 154(b) by 0 days.

(21) Appl. No.: 12/721,909

(22) Filed: Mar. 11, 2010

(65) Prior Publication Data
US 2010/0163643 A1 Jul. 1, 2010

Related U.S. Application Data

(63) Continuation of application No. PCT/EP2007/061673, filed on Oct. 30, 2007.

(51) Int. Cl.
*A61L 9/04* (2006.01)
(52) U.S. Cl. .......... 239/6; 239/34; 239/53; 239/55; 239/57; 239/289; 428/905; 223/86; 206/0.5
(58) Field of Classification Search ............ 239/34, 239/53, 55–59, 289, 6; 428/905; 223/86; 223/89; 206/0.5
See application file for complete search history.

(56) References Cited

U.S. PATENT DOCUMENTS

| 3,613,994 | A | 10/1971 | Goodman |
| 5,975,427 | A | 11/1999 | Harries |
| 6,902,817 | B2 | 6/2005 | Bowen et al. |
| 7,028,917 | B2 * | 4/2006 | Buthier .......... 239/34 |
| 7,530,503 | B2 * | 5/2009 | Caserta et al. .......... 239/57 |
| 2005/0199740 | A1 * | 9/2005 | Harris, Jr. .......... 239/34 |
| 2006/0102737 | A1 * | 5/2006 | Harmon et al. .......... 239/53 |
| 2007/0194368 | A1 | 8/2007 | Caserta et al. |

FOREIGN PATENT DOCUMENTS

| DE | 25 33 235 | 2/1977 |
| DE | 3715359 | 12/1988 |
| ES | 2163668 | 12/1997 |
| GB | 2275609 | 9/1994 |
| WO | 98/23304 | 6/1998 |
| WO | 01/56900 | 8/2001 |

OTHER PUBLICATIONS

International Search Report for corresponding International Application No. PCT/EP2007/061673 with a mailing date of Feb. 15, 2008.
International Preliminary Report on Patentability for corresponding International Application No. PCT/EP2007/061673 issued Oct. 20, 2009.

* cited by examiner

*Primary Examiner* — Steven J Ganey
(74) *Attorney, Agent, or Firm* — Myers Wolin, LLC

(57) ABSTRACT

A thermoformed container is provided for evaporating volatile substances, which is provided with means enabling such container to withstand high temperatures without experiencing deformations which deteriorate its functionality or appearance. The container has a reinforcing film having a deformation temperature exceeding the plastic material sheet with which the container is obtained. Also disclosed is a method for manufacturing said container.

5 Claims, 3 Drawing Sheets

CONTAINER FOR EVAPORATING VOLATILE SUBSTANCES AND METHOD OF MANUFACTURING SAID CONTAINER

CROSS REFERENCE TO RELATED APPLICATIONS

This is a continuation under 35 U.S.C. 120 of International Application PCT/EP2007/061673 filed Oct. 30, 2007, which claims priority to Spanish Patent Application No. P200702433 filed Sep. 12, 2007, the contents of each of which are incorporated herein by reference.

OBJECT OF THE INVENTION

The present invention generally relates to a construction for reinforcing objects obtained by thermoforming to enable them to withstand a higher temperature. More specifically, the invention relates to a thermoformed container for evaporating volatile substances, which is provided with means enabling the same to withstand high temperatures without experiencing deformations which deteriorate its functionality or appearance.

The invention allows that this type of containers can be used in spaces where high temperatures can be reached, such as inside a vehicle, without considerably increasing their manufacturing cost.

The invention also relates to a method for manufacturing said container.

BACKGROUND OF THE INVENTION

Devices are known for diffusing volatile substances consisting of a container obtained by thermoforming. This type of containers is obtained by joining, on one hand, a thermoformed film, and on the other hand, a preferably flat "diffusion" film through which the substance is released. The space between both films forms the actual container of the substance to be evaporated in liquid, solid (for example gel) form, or impregnated in a porous solid in the container.

The diffusion film has the function of retaining the volatile substance in its liquid or solid form but letting it pass through in its vapor form. It can consist of a semi-permeable membrane, which lets the vapor pass through but is impermeable to liquid, or it can consist of a perforated film which retains a solid but lets its vapor pass through.

The diffusion film is usually covered by an impermeable film which is removed before the first use of the product, and the purpose of which is to prevent the release of the substance during the storage period.

An example of the construction of this type of devices can be found in patents WO9823304A1 or U.S. Pat. No. 6,902,817.

In its simplest embodiment, this type of product has a hook for hanging it in a certain space (a closet rod, the rearview mirror of a car, a metallic structure of a dishwasher, etc).

The possibility of carrying out this type of hook directly in the thermoformed film, which has the advantages of a simpler manufacturing process and a lower cost, is also known.

A known improvement for this type of hook in the thermoformed material is to carry out a mechanical reinforcing embossment during the thermoforming process, whereby obtaining the cavity to be able to offset the low rigidity of the film. An example of this technique is described in U.S. Pat. No. 3,613,994.

This type of devices, however, has the drawback arising when subjected to high temperatures, for example exceeding 70°, which can occur, for example, inside an automobile under the direct impingement of the sun or in the dishwasher. This is primarily because the materials normally used for the thermoforming process are low-temperature processing plastic materials, which are formed at temperatures under 120° C., and even under 100° C. The films to be thermoformed are generally multilayer structures essentially having a core material providing the appearance and the mechanical rigidity to the film, a sealing material for being able to be joined by welding to the diffusion film and other adhesive or barrier layers.

The thermoforming process furthermore usually causes significant residual stress in the same thermoformed film which, when subjected to a certain temperature, causes the film to tend to recover its initial flat shape, causing the distortion of the thermoformed shape. This deformation can be observed at the level of the thermoformed cavity, but it is more critical at the level of the mechanical reinforcing rib of the hook, which can cause the product to fall.

An obvious solution to this problem can be the use of materials having a higher thermal resistance, but this would involve an increase in the process temperatures (which could further be incompatible with the presence of volatile materials in the container) and an increase in the raw material cost.

Another solution could be to use a more robust hook obtained for example by molding, by injection or by manufacturing it out of cardboard. However, this involves an additional process of manufacturing the hook and an assembly process, which involves a significant additional cost. Spanish patent ES-2163668 is an example of this solution.

Hook or hanging systems produced with cardboard, injected plastic or casings injected in plastic with a built-in hook and containing therein the product applied with a membrane are known, and these would also withstand 70° C. but are not carried out with a single process and with only two components.

Therefore, there is a need in the state of the art for a thermoformed container resistant to high temperatures and which can be obtained at a very low manufacturing cost.

DESCRIPTION OF THE INVENTION

The present invention solves the aforementioned technical problem by means of the inventive subject-matter comprised in the attached independent claims.

Therefore, a first aspect of the invention relates to a container for evaporating volatile substances, which is formed by a thermoformed sheet in which an outer face and an inner face are defined, a cavity or receptacle suitable for housing a volatile substance to be evaporated, as well as a supporting part adapted shape-wise to suitably position the device during its normal use being formed in said sheet. Said supporting part conventionally has a depression providing it with mechanical rigidity.

The container is characterized in that at least one portion of said supporting part is provided, joined in an integral manner, with an element resistant to heat deformation, and which maintains the rigidity of that supporting area even when it is subjected to high temperatures. More specifically, said element consists of a film fixed on at least one part of one of the faces corresponding to the supporting part, said reinforcing film having a deformation temperature exceeding the deformation temperature of said sheet, i.e. the reinforcing film is resistant to heat deformation, when it is subjected to the temperature at which the mentioned thermoformed sheet deforms due to the heat.

By the expression a deformation temperature exceeding the deformation temperature of the thermoformed sheet, it is understood that said reinforcing film is either obtained in a material the intrinsic deformation temperature of which exceeds the deformation temperature of the material of the thermoformed sheet, or it is free of residual stress which would involve its deformation at a temperature of less than the intrinsic temperature, or both.

The mentioned supporting part preferably has the shape of a hook and is arranged at one end of the device such that it can be hung, for example, from a closet rod or the rearview mirror of an automobile.

In other embodiments of the invention, said supporting part can adopt other shapes which allow suitably positioning the container during its normal use.

The reinforcing film can be applied for materials to be thermoformed with a thickness comprised between micron counts of 200 μm and 1000 μm. The reinforcing film is insensitive to high temperatures and does not experience a stress relief at these temperatures because there is no residual stress, since it has not been subjected to any thermoforming process.

The entire structure is thus supported in a hook shape to reduce or even eliminate the torsion effect exerted by the residual stress relief in the hook when it is subjected to high temperatures.

Another aspect of the invention relates to a method of manufacturing containers for evaporating volatile substances with the features of the previously described container.

DESCRIPTION OF THE DRAWINGS

To complement the description being made and for the purpose of aiding to better understand the features of the invention according to a preferred practical embodiment thereof, a set of drawings is attached as an integral part of said description which, with an illustrative and non-limiting character, shows the following.

PREFERRED EMBODIMENT OF THE INVENTION

Figure 1:
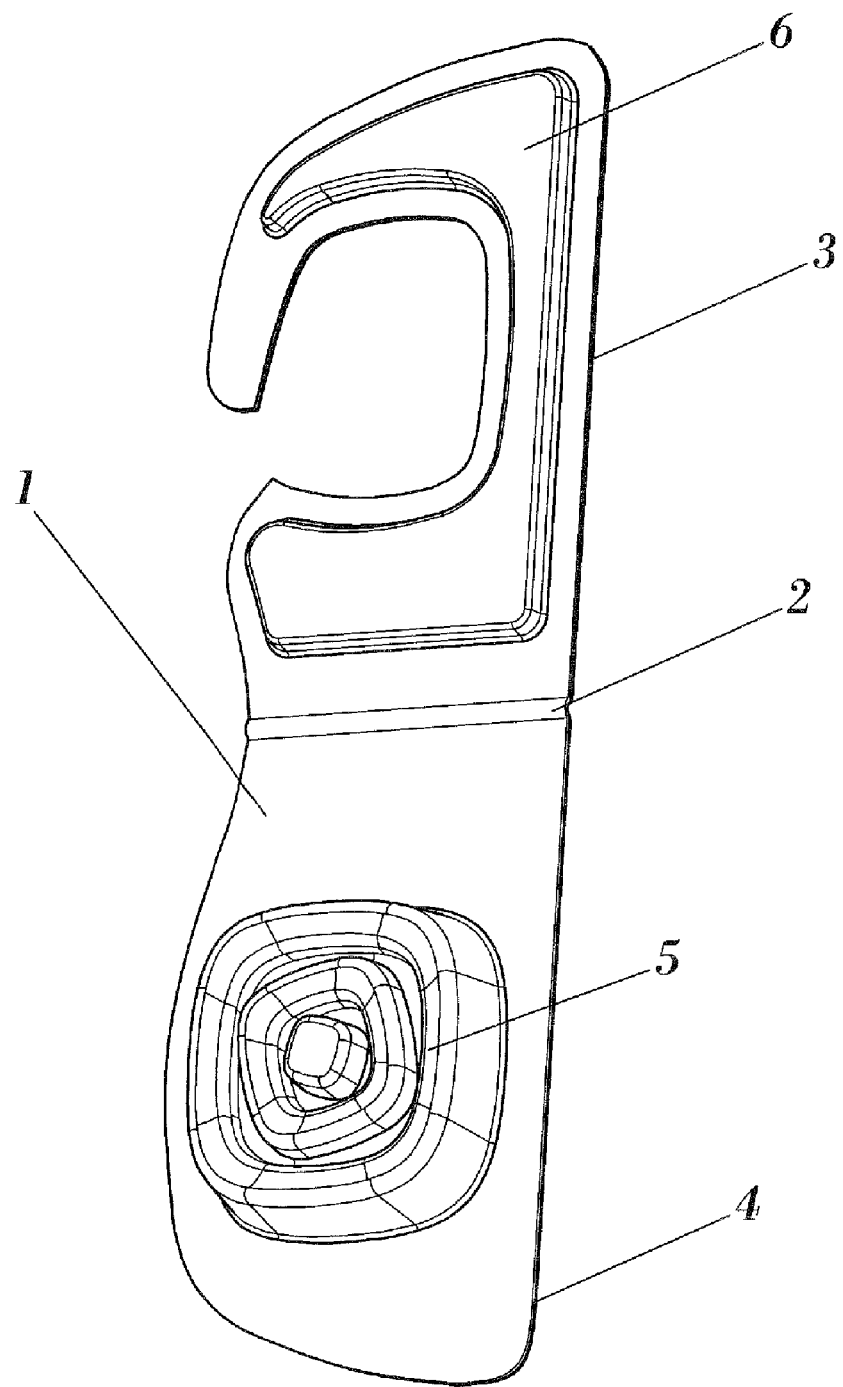
FIG. 1 shows a front perspective view of an embodiment of the container object of the invention.

In view of FIG. 1, it can be seen how the container object of the invention in one of its possible embodiments, is formed by a thermoformed plastic sheet (1) in which two parts are defined, in this case such parts differentiated by a fold (2) allowing the inclination of one part of the container with respect to the other part. A first part (4) thus has a cavity or receptacle (5) defining the actual container intended for containing a volatile substance of any type.

In addition, a second part (3) forms the supporting part of the container, given that this is the part that is formed to position such containing in a certain position during its normal use. In this case, this supporting part has the shape of a hook as can be seen in the figures, and it has a depression (6) providing rigidity to said part.

The cavity (5) and the depression (6) have been obtained during the thermoforming of the film (1), deforming it towards the same side of the sheet that can be referred to as the outer face thereof. The other face of the sheet (1) is flat and is covered by a semi-permeable membrane (7) which, in this case, covers the entire extend thereof, as can especially be seen in FIG. 2. However, in other embodiments, the membrane could cover just the part (4) corresponding to the actual container.

Based on this known structure, the container object of the invention is characterized in that it incorporates a reinforcing film (8) adhered on one of the faces of the supporting area (3), in this case in the inner face. This reinforcing film is preferably made of metal, such as aluminum for, so its deformation temperature, i.e. the temperature at which it deforms, exceeds the deformation temperature of said sheet.

The reinforcing film (8) is arranged on the entire rear face of the supporting area (3), whereas a peelable film (9) covering the membrane (7) is arranged in the other part of the container.

The invention also relates to a method of manufacturing containers for evaporating volatile substances, in which a plastic material sheet (1) is thermoformed to obtain in said sheet a cavity (5) suitable for housing a volatile substance, and a supporting part of the container with a depression providing rigidity to said part.

The material to be thermoformed is a 500 micron thick film of polyester/polyethylene, i.e. PET/PE, in which the PE is the welding layer.

A multilayer film comprising a semi-permeable membrane on its face closest to the thermoformed sheet and a reinforcing film is applied to the mentioned sheet. The reinforcing film has a deformation temperature exceeding the deformation temperature of the sheet.

The multilayer film is preferably joined to the thermoformed sheet by means of heat-welding both around the cavity of the container and around the depression of the supporting part.

In a preferred embodiment, the reinforcing film is made of aluminum.

Figure 2:
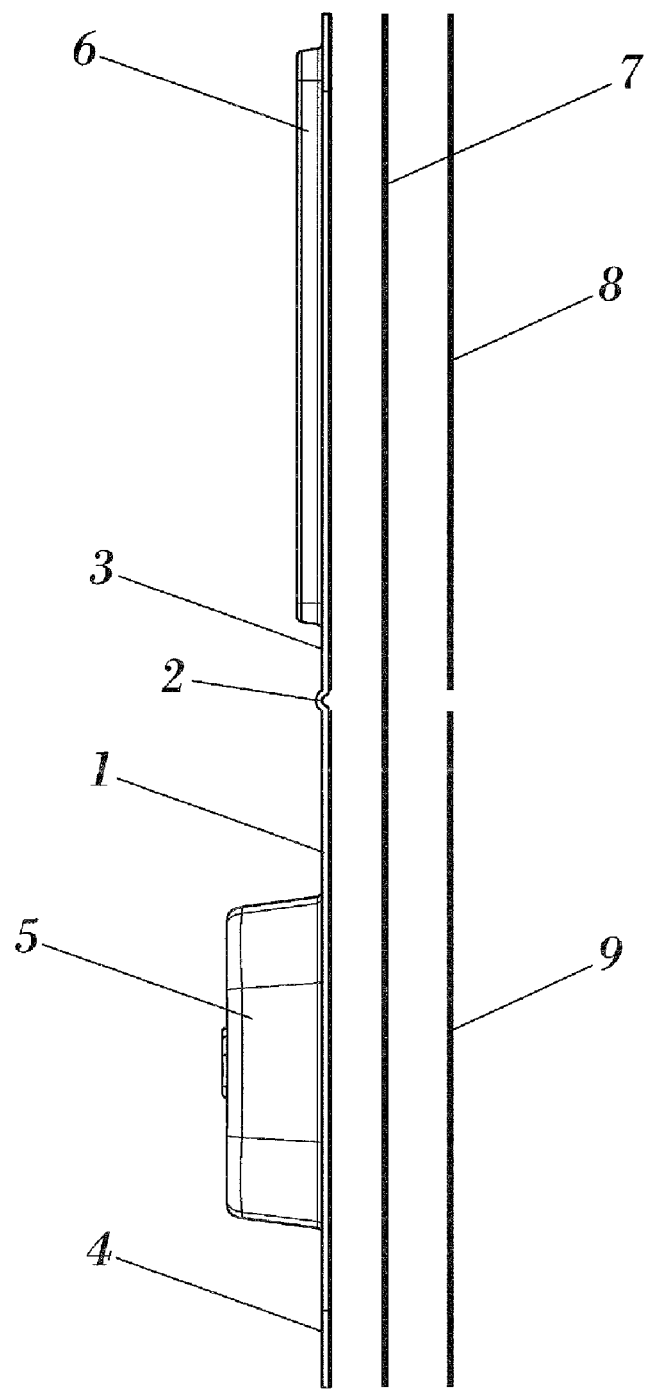
FIG. 2 shows a side view of the container of FIG. 1, with the semi-permeable film and the reinforcing film separated to make seeing them easier.
Figure 3:
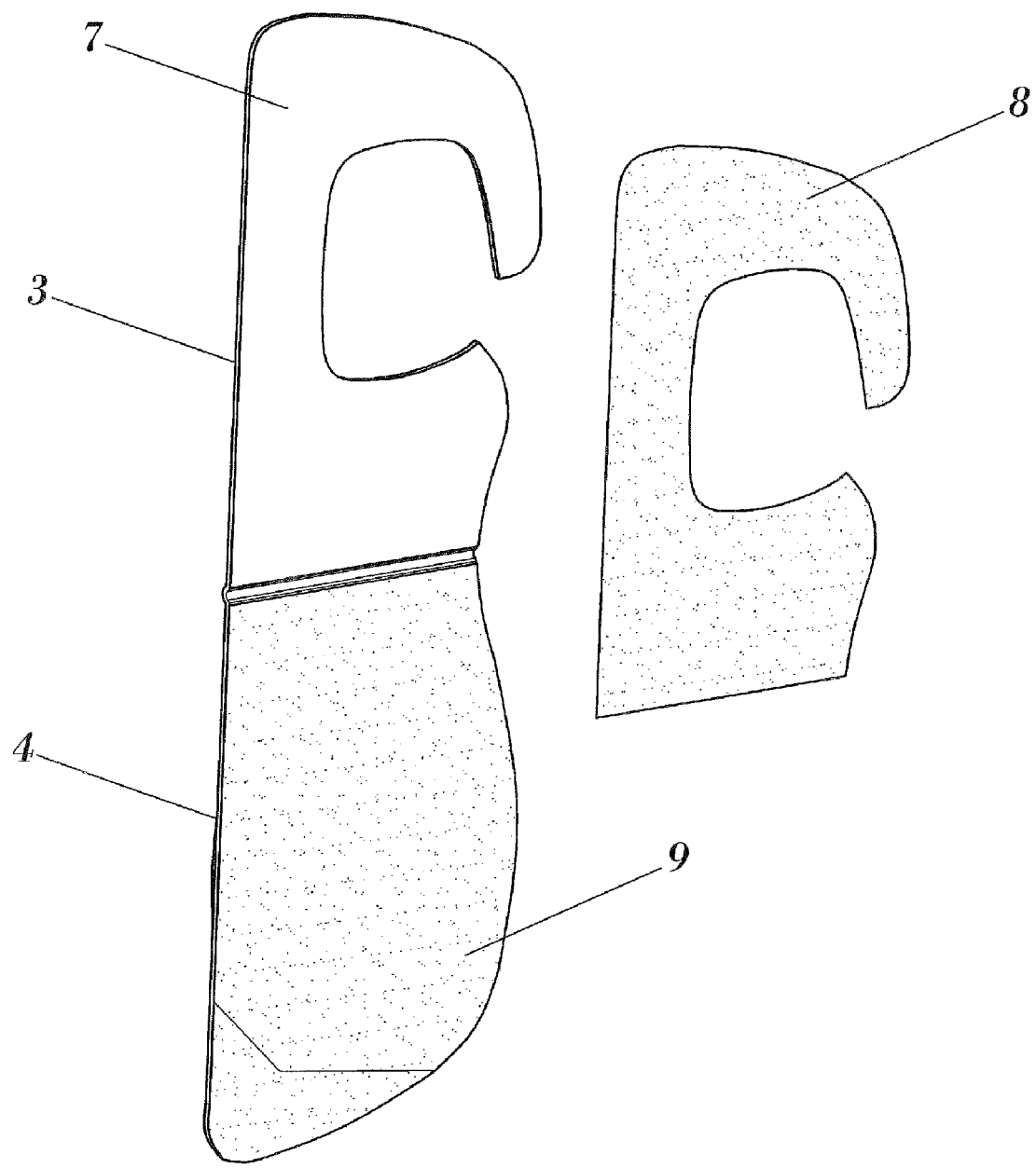
FIG. 3 shows a rear perspective view of the container of FIG. 1, with the reinforcing film separated.

A cut is made in said film multilayer to separate the part of the film that is arranged on the supporting part (3) from the part of the film arranged on the cavity, as can be seen in FIG. 2.

The film arranged on the cavity is useful as a peelable film preventing the product from evaporating during storage and transport. Therefore, when the seal is removed from the aluminum, the product is released only in the part of the container.

The nature of the reinforcing film is therefore identical to the peelable film covering the container of the volatile substance.

The film can also be exactly the same and even come from the same reel which is applied at the same time in both parts of the container and is then separated by cutting the film.

A cut is finally made on said sheet and reinforcing film, according to a perimetral contour predefined around the cavity and the supporting part to obtain the end product as it is seen in FIG. 1.

Different possibilities of practical embodiments of the invention are described in the attached dependent claims.

In view of this description and set of drawings, a person skilled in the art will be able to understand that the embodiments of the invention that have been described can be combined in many ways within the object of the invention. The invention has been described according to several preferred embodiments thereof, but it will be obvious for a person skilled in the art that many variations can be introduced in said preferred embodiments without exceeding the object of the claimed invention.

The invention claimed is:

1. A container for evaporating volatile substances, formed by a thermoformed sheet in which an outer face and an inner face are defined, a cavity being formed in said sheet containing a volatile substance, as well as a supporting part adapted in shape to suitably position the container during its use, said supporting part having a depression providing rigidity to said part, wherein said supporting part of the container has a reinforcing film which has a deformation temperature greater than the deformation temperature of said sheet, the reinforcing film being integrally joined at least in part of one of the faces of the supporting part to the extent that the reinforcing film can maintain the rigidity of said supporting part when it is subjected to high temperatures.

2. A container according to claim 1, wherein the reinforcing film is a non-thermoformed body.

3. A container according to claim 1, wherein said supporting part has the shape of a hook and is arranged at one end of the container.

4. A container according to claim 1, wherein the reinforcing film contains a metallic layer.

5. A method of manufacturing containers for evaporating volatile substances, comprising the operative steps of thermoforming a plastic material sheet to obtain in said sheet at least one cavity to house a volatile substance, and a supporting part adapted in shape for position the container during its use, providing said supporting part with a depression providing rigidity to said part, arranging a multilayer film comprising a semi-permeable membrane and a reinforcing film, wherein the semi-permeable membrane is arranged on the face of the multilayer film closest to the thermoformed sheet, and wherein said reinforcing film has a deformation temperature greater than the deformation temperature of said sheet, joining the multilayer film to the thermoformed sheet by means of heat-welding both around the cavity of the container and around the depression of the supporting part, such that said multilayer film closes said cavity, making a cut in said multilayer film separating the part of the film that is arranged on the supporting part of the part of the film arranged on the cavity, and making a cut on said sheet and reinforcing film according to a predefined contour.

* * * * *